: US005879159A

United States Patent [19]
Cipolla

[11] Patent Number: 5,879,159
[45] Date of Patent: Mar. 9, 1999

[54] PORTABLE HIGH POWER ARC LAMP SYSTEM AND APPLICATIONS THEREFOR

[75] Inventor: John C. Cipolla, Trout Run, Pa.

[73] Assignee: Ion Laser Technology, Inc., Lester, Pa.

[21] Appl. No.: 772,964

[22] Filed: Dec. 24, 1996

[51] Int. Cl.$^6$ .................................................. A61C 5/00
[52] U.S. Cl. ........................... 433/29; 433/215; 362/183; 362/804
[58] Field of Search ............................. 433/29, 229, 215; 362/183, 804

[56] References Cited

U.S. PATENT DOCUMENTS

| | | | |
|---|---|---|---|
| 3,621,322 | 11/1971 | Rehmet et al. | 313/184 |
| 3,635,537 | 1/1972 | Miller et al. | 315/145 |
| 3,636,401 | 1/1972 | Cortorillo et al. | 313/352 |
| 3,644,768 | 2/1972 | McRae | 313/44 |
| 3,660,711 | 5/1972 | Stanyon et al. | 313/220 |
| 3,675,068 | 7/1972 | Strauss | 313/217 |
| 3,715,613 | 2/1973 | Parkman | 313/636 |
| 3,769,544 | 10/1973 | Miller | 313/175 |
| 3,808,496 | 4/1974 | McRae et al. | 313/113 |
| 3,881,132 | 4/1975 | Miller | 315/344 |
| 3,930,504 | 1/1976 | de Laforcade | 350/206 |
| 3,949,258 | 4/1976 | Soodak | 313/25 |
| 3,970,883 | 7/1976 | Lavering | 313/39 |
| 3,984,590 | 10/1976 | Mason et al. | 427/106 |
| 4,179,037 | 12/1979 | Chan et al. | 313/113 |
| 4,266,180 | 5/1981 | Juvan | 322/4 |
| 4,481,443 | 11/1984 | Mathijssen | 313/636 |
| 4,536,832 | 8/1985 | Lemmons | 362/264 |
| 4,599,540 | 7/1986 | Roberts | 313/570 |
| 4,633,128 | 12/1986 | Roberts et al. | 313/113 |
| 4,658,179 | 4/1987 | Roberts | 313/113 |
| 4,661,070 | 4/1987 | Friedman | 433/229 |
| 4,686,419 | 8/1987 | Block et al. | 313/641 |
| 4,702,716 | 10/1987 | Roberts | 445/26 |
| 4,724,352 | 2/1988 | Schuda et al. | 313/246 |
| 4,757,427 | 7/1988 | Oostvogels et al. | 362/32 |
| 4,785,216 | 11/1988 | Roberts et al. | 313/32 |

(List continued on next page.)

FOREIGN PATENT DOCUMENTS

| | | |
|---|---|---|
| 2 223 085 | 11/1972 | Germany . |
| 3616329 | 11/1986 | Germany . |
| 77-2443Y | 7/1976 | U.S.S.R. . |
| 88-104642 | 9/1987 | U.S.S.R. . |
| 91-021059 | 5/1990 | U.S.S.R. . |

OTHER PUBLICATIONS

EG&G Electro–Optics Flashlamp Operations Manual.
Cermax focused Xenon Lamps ILC Technology Jul. 1995, ILC–128.
Luxtrak UV nd Visible (470 nm blue) Light Curable Adhesives.
Radiation Curing of Coatings with Xenon Lamps Barbara Howell, Michael O'Donnell Modern Paint and Coating Apr. 1995.
USHIO, Discharge Lamps, 93–12–40000YA.
USHIO, 300 Series, S–UXR300.
Cermax, Xenon Illuminators and Systems, ILC Technology.
Opti–Forms, Inc., Electroformed Optics & High Performance Coatings ©1992.
Ultra–life, Short Arc Xenon Lamps, ORC.
Cermax, Xenon Illuminators, ILC Technology.

Primary Examiner—Cary E. O'Connor
Attorney, Agent, or Firm—Weil, Gotshal & Manges, LLP

[57] ABSTRACT

A portable, high power arc lamp system for composite curing and tooth whitening applications utilizes battery cells to power a lamp, such as a short-arc xenon lamp. The use of battery power allows for a high power system without the need for costly components required if ac power were used. Battery power is acceptable for low duty cycle applications such as composite curing and tooth whitening. The batteries may be recharged using either standard 110 V or 220 V house current and a charging circuit is included to charge the batteries. An elliptical reflector is used to direct the light from the xenon lamp to a flexible light guide. The system of the present invention is particularly suited to the curing of dental composites and tooth whitening procedures. Significantly improved methods of curing and whitening may be realized through the use of a high power light source of the present invention.

31 Claims, 3 Drawing Sheets

U.S. PATENT DOCUMENTS

| | | | |
|---|---|---|---|
| 4,823,043 | 4/1989 | Roberts et al. | 313/213.61 |
| 4,836,782 | 6/1989 | Gonser | 433/229 |
| 4,847,530 | 7/1989 | English et al. | 313/25 |
| 4,940,922 | 7/1990 | Schuda et al. | 315/246 |
| 5,072,158 | 12/1991 | Shuda | 315/276 |
| 5,299,279 | 3/1994 | Roberts | 392/421 |
| 5,329,436 | 7/1994 | Chiu | 362/294 |
| 5,399,930 | 3/1995 | Roberts | 313/46 |
| 5,414,600 | 5/1995 | Strobl et al. | 362/32 |
| 5,418,420 | 5/1995 | Roberts | 313/114 |
| 5,430,634 | 7/1995 | Baker et al. | 362/32 |
| 5,446,818 | 8/1995 | Baker et al. | 385/78 |
| 5,452,392 | 9/1995 | Baker et al. | 385/92 |
| 5,471,129 | 11/1995 | Mann | 433/141 |
| 5,509,095 | 4/1996 | Baker et al. | 385/31 |
| 5,530,632 | 6/1996 | Shikano et al. | 433/29 |

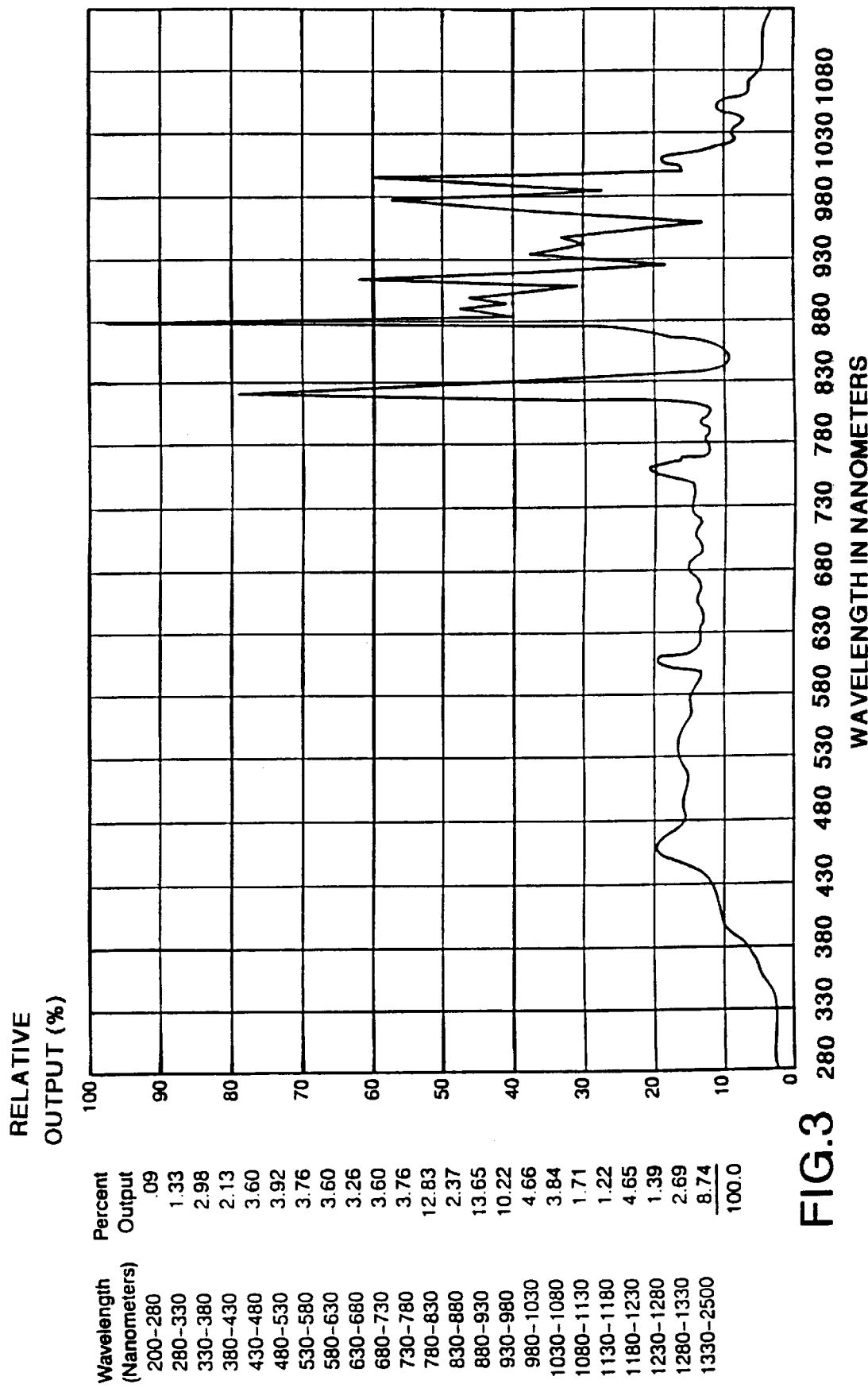

PORTABLE HIGH POWER ARC LAMP SYSTEM AND APPLICATIONS THEREFOR

BACKGROUND OF THE INVENTION

This invention relates to a portable, high power arc lamp system. More particularly, this invention relates to a battery powered, high power, arc lamp system suited for low duty cycle applications such as photocurable composite and resin curing and tooth whitening. The lamp may be a short arc xenon, argon, or utilize another gas. The invention further relates to using a system of the present invention to cure photocurable materials and in tooth whitening procedures.

Arc lamps, particularly short arc xenon lamps, are known in the art for various applications, such as infrared and visual searchlights, fiber optic illumination, spectroscopy, stadium lighting, stage and screen lighting, automobile headlights, and microscopy. The spectral distribution of xenon lamps is similar to that of natural daylight.

Arc lamps have also been utilized for composite and resin curing applications. For example, U.S. Pat. No. 5,290,169 to Friedman et al. discloses a hand held light curing gun for curing dental composites. The lamp may be tungsten/halogen, mercury vapor, short arc xenon, or metal-halide. An optical light guide is used to transmit the light output by the lamp to the dental restoration. U.S. Pat. No. 4,948,215 to Friedman also discloses a hand held dental curing light used in combination with an optic light guide selected from a plurality of autofocus optic light guides for transmitting maximum power density to different sized dental materials.

Existing dental curing lamps are used in conjunction with photocurable dental materials that replace gold, porcelain, and silver amalgam. However, the power output of such systems is relatively low, so that curing can take a substantial amount of time. The lower the power output, the longer it takes to cure the composite. In addition, the photocurable materials used in dental applications generally exhibit improved properties when they are cured at a faster rate. Furthermore, as discussed herein, it has been found that resins and composites cured at higher power levels require less total energy than those cured at lower power levels. Thus, there is a need for a high power dental curing lamp that is compatible with existing dental office operatories.

In addition, the use of light, and in particular light in the blue/green spectrum, is beneficial in tooth whitening procedures because light in this wavelength tends to be more readily absorbed by yellow/brown colored stain molecules but mostly reflected by the red colored tooth pulp in vital teeth. One such tooth whitening procedure utilizes a whitening agent, such as a peroxide compound, in combination with laser light from an argon laser to generate free oxygen radicals to accelerate the whitening process. Such procedures, however, can require a lengthy office visit due to the amount of time each tooth must be exposed to laser light in order to effectuate the whitening process. This is because the argon lasers used in these procedures typically have output powers in the range of 250 mW–500 mW.

U.S. Pat. No. 4,661,070 to Friedman discloses a method for bleaching discolored teeth using a concentrated solution of hydrogen peroxide and a source of light comprising ultraviolet energy in the 320 to 420 nanometer range and infrared energy in the 700 to 1200 nanometer range. The lamp may be tungsten halogen, mercury vapor, short-arc xenon, or metal halide. An elliptical reflector directs the light into a light guide. Friedman, however, does not disclose the use of a high power lamp and in fact does not mention power levels or exposure times. Moreover, Friedman filters out light in the 420 to 700 nanometer range, i.e., visible light, which applicants have found to be most beneficial for both curing and tooth-whitening applications, as discussed above.

In order to reduce the time required to effect composite curing as well as tooth whitening, a higher power light source is needed. In particular, a light source with a power input of 1500–3000 W is desirable.

Several problems exist, however, in designing such a system utilizing 110 V alternating current, the standard house current in the United States that is typically available in dental offices. First, many building codes impose limits on the permissible current draw of electrical appliances, which therefore limits the maximum power output of an arc lamp system. Thus, to obtain high power outputs, it is typically necessary to use 220 V to reduce current draws. However, 220 V power is typically not readily available in dental office operatories and other office settings. In addition, to the extent higher power outputs can be achieved using standard house current, costly linear or inverter power supplies are required in order to provide a low voltage, high current output suitable to drive an arc lamp. This is because arc lamps require specially designed power supplies tailored to the starting and operational requirements of the lamp, with limits on in-rush current and peak-to-peak current ripple. Moreover, even if 220 V power is available, there remains the problem of power spikes and ripple that result from the use of ac power and can shorten the life of arc lamps.

In dental curing and tooth whitening applications, the energy requirements are determined in accordance with a total amount of energy to be imparted to a given tooth. Typically, 20 joules of total energy per tooth is the maximum energy provided for both curing and tooth whitening applications. This figure is used to ensure that the pulp in vital teeth is not damaged. Existing curing lamps and lasers used for curing and whitening procedures generally operate at power levels of less than 1 watt. Thus, it takes in the range of 20–60 seconds to impart the required amount of energy to a tooth.

Both curing and whitening procedures can be improved through the use of higher power light sources that reduce the exposure time required per tooth application. This is because photocurable composites and resins typically exhibit improved properties the faster they are cured. Similarly, with regard to whitening procedures using peroxide compounds, the bleaching efficiency of the peroxide is improved because as more energy is applied, more of the peroxide is broken down into free oxygen radicals. The longer the peroxide is resident on a tooth, the greater the amount of molecular oxygen produced, which does not have nearly the same bleaching effect as free oxygen radicals.

Therefore, there is a need for a high power arc lamp system for curing composites and resins as well as tooth whitening applications.

In addition, there is a need for an improved procedure for both composite and resin curing where the composites and resins are cured at a higher power level to both reduce the cure time and improve the properties of the cured material.

There is additionally a need for an improved tooth whitening procedure using a high power light source to both reduce the duration of the whitening procedure and improve the effectiveness of the bleaching compositions.

SUMMARY OF THE INVENTION

In accordance with the present invention, a high power, battery operated arc lamp system is provided, particularly suited for composite curing and tooth whitening applications. Battery packs are used as the power source for the lamp so that the system is both portable and may be recharged using standard 110 V house current. In addition, the use of battery power enables the system to be readily moved from one office to another. Furthermore, the use of batteries and charging circuitry is much less costly system than a linear or inverter power supply operating from ac power. The battery packs and associated circuitry are chosen based on the expected duty cycle and total use of the system in a single day so that battery pack life is maximized and the batteries may be recharged overnight. While in operation, the system need not be supplied with ac power to recharge the batteries and thus may be freely moved about an office. Another advantage of using battery power is that batteries provide a very stable output with no power spikes or ripple, which provides an improvement over both 110 V and 220 ac power. The use of batteries also increases the life of the arc lamp and allows for a smaller overall system as compared with ac power.

Also in accordance with the present invention, an improved method for curing resin and composite materials is disclosed wherein such materials are cured by exposing them to light energy from a portable, high power, arc lamp system. Materials cured in accordance with the method of the present invention have been shown to exhibit improved properties and require less total energy as compared with the same materials cured with prior art curing systems.

Also in accordance with the present invention, an improved method for whitening teeth is disclosed wherein a bleaching composition is applied to a tooth to be whitened and the tooth is exposed to light energy from a portable, high power, arc lamp system. The use of the tooth whitening procedure of the present invention provides for more effective whitening of a tooth in a shorter time period as compared with prior art tooth whitening methods.

The present invention thus provides an economical, high power, battery operated arc lamp system with many different applications. The output of the lamp is optically coupled to a light guide to enable the operator of the lamp to direct the light to a desired location. The high power output substantially reduces the time required for curing dental and other composites as well as whitening teeth. In addition, the use of battery power allows the system to be used with standard 110 V house current without the need for high cost components. A charging circuit recharges the batteries at a sufficient rate to fully charge the batteries overnight. The invention has particular application to photoactivated dental restorative materials, resins, composites, coatings, as well as a variety of industrial applications including potting electrical components and cementing polycarbonate tubing. The invention also has application in tooth whitening procedures, and may also be used for other low duty cycle operations as well.

Although high power outputs are desirable for curing and whitening applications, the total energy requirements for these applications are low. Therefore, the duty cycle for the arc lamp system is also low, enabling the use of battery power without the need for ac power backup as is the case for prior art arc lamps used for continuous operation. For example, if each tooth requires only about 1 second or less of exposure time, the system need be in operation only for a maximum of about 30 seconds to whiten all of a patient's teeth. For dental curing applications, the total usage time is even less, as only 1 or 2 teeth are typically treated at a time. For the same reasons, the duty cycle for industrial applications is also low enough to permit use of the system for extended periods without recharging.

BRIEF DESCRIPTION OF THE DRAWINGS

The foregoing summary, as well as the following detailed description of a preferred embodiment, is better understood when read in conjunction with the drawings appended hereto. For purposes of illustrating the invention, there is shown in the drawings a presently preferred embodiment, it being understood, however, that the invention is not limited to the specific instrumentalities and components disclosed herein.

FIG. 3 is an illustration of the relative spectral intensity of a short-arc xenon lamp.

DETAILED DESCRIPTION OF THE INVENTION

The present invention is a high power, portable arc lamp system with applications for photoactivated dental restorative materials, resins, composites, coatings, as well as a variety of industrial applications including potting electrical components and cementing polycarbonate tubing. The invention also has application in tooth whitening procedures, and may also be used for other low duty cycle operations as well. In a preferred embodiment, a short arc xenon arc lamp is used because of its relatively flat spectral distribution in the visible range. It has been found that visible light, particularly in the blue/green spectrum, is useful both for curing and tooth whitening applications. An optical filter is used to provide output light primarily in the blue range, i.e., approximately 500 nanometer wavelength.

Figure 1:
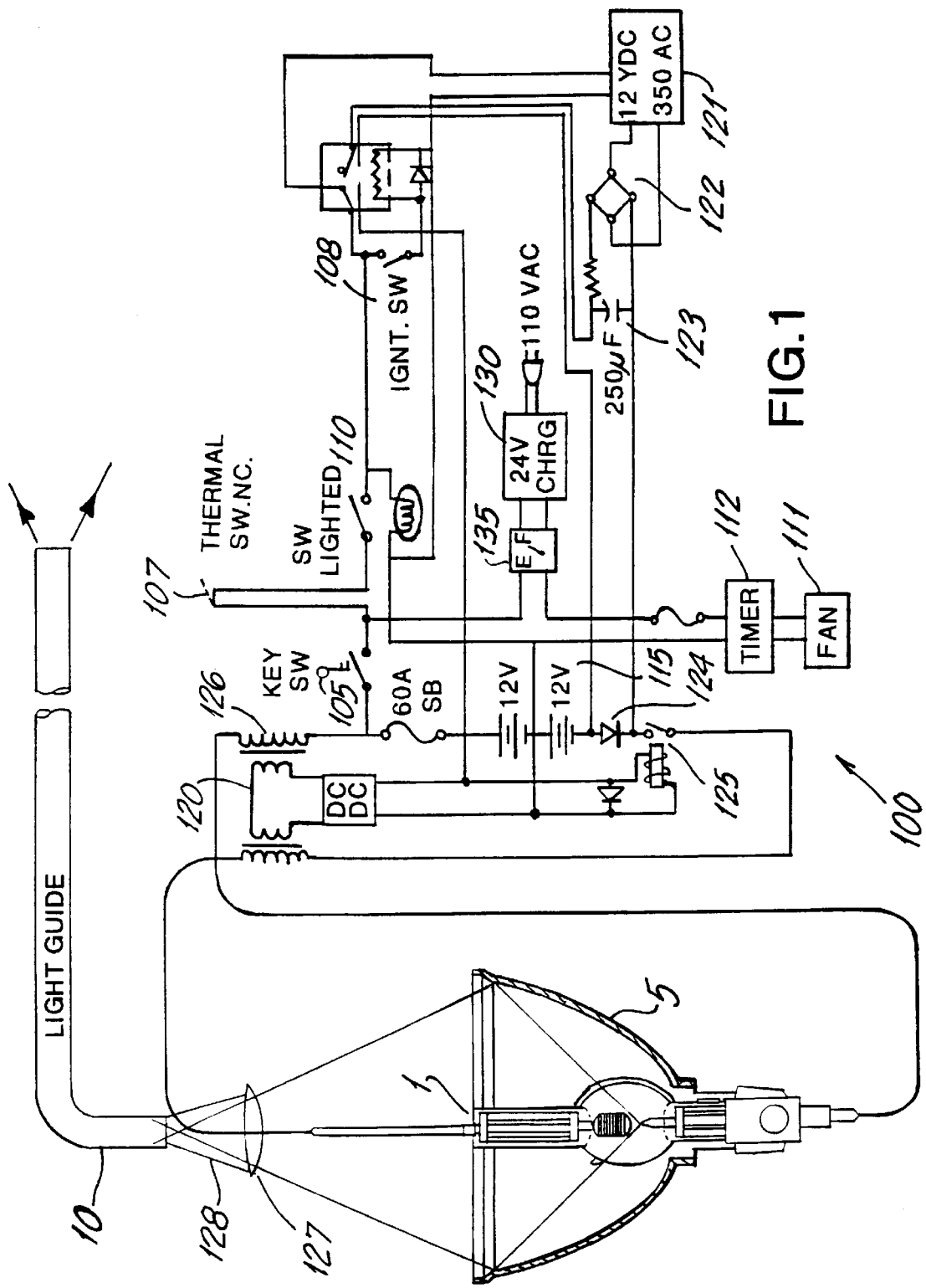
FIG. 1 is a schematic diagram of the arc lamp system of the present invention.

FIG. 1 is a schematic diagram of a preferred embodiment of the present invention. A short arc xenon lamp (rated at 1600 W) with an ellipsoidal reflector 5 is shown with its output focused at the input of a light guide 10. Those of ordinary skill in the art will recognize that other types of reflectors may be used. The reflector may be made from a metal or glass, as will be recognized by those of skill in the art. An example of a suitable xenon short arc lamp is the Ultralife™ model XM1600-27HS manufactured by Optical Radiation Corp. of Azusa, Calif. It is also possible to use higher powered lamps, such as one rated at 2000 W or 3000 W, so as to further reduce the required exposure time. In a preferred embodiment, the reflector 5 includes a dichroic coating to absorb infrared energy. If the reflector is glass, the infrared energy will then be passed through the reflector and dissipated as radiant energy. If a metal reflector is used, the infrared energy will absorbed by the reflector and may be dissipated through cooling fins or the like. When used for its intended applications as described herein, however, minimal cooling is required due to the very low duty cycle of the device.

The circuitry for operating the lamp is shown generally as 100. Due to safety considerations, a key switch 105 is used to enable the lamp system for operation. In addition, lighted power switch 110 is wired in series with the key switch for turning on the system and indicating power on. A thermal switch 107 is shown between the key and power switches to automatically open the circuit if the temperature of the housing exceeds a predetermined value. Due to the high power output, the housing of the lamp system can become hot if the system is used for continuous operation. Fan 111 is used to cool the lamp system housing and is operated for a period of time after the system is turned off under control of timer 112. The fan may not be necessary, however, because little heat is dissipated when the system is used for its intended low duty cycle applications. Switch 108 is an ignition switch for activation of the lamp.

Two 12 V, lead acid battery packs 115, each with a capacity of 12 amp-hours are used to provide power to the lamp. In a preferred embodiment, model PS-12120 batteries from Power-Sonics Corp. are used. Because short arc xenon lamps require a higher ignition voltage than a steady state voltage, a power converter 120 is used to provide the ignition voltage of at least 25 kilovolts. High voltage transformer 126 injects the high voltage across the arc lamp 1. A charging circuit 130 is used to charge the batteries using 110 V house current. In a preferred embodiment, an LS Series Microprocessor Charger, made by Interacter, Inc., is used. An energy meter 135 is used to determine the state of the batteries. The batteries provide a power source for the arc lamp with virtually no ripple.

Items 121 and 122 comprise a power converter used to produce a minimum of 300 V (termed the boost voltage), which is used to sustain the arc just after the lamp has been ignited by the ignition voltage. Boost capacitor 123 stores the boost voltage energy and hold-off diode 124 permits the lamp to be operated at the boost voltage after ignition, but permits the flow of current from the batteries after the capacitor 123 discharges. High current relay 125 provides for disconnection of the battery packs from the arc lamp 1.

Figure 2:
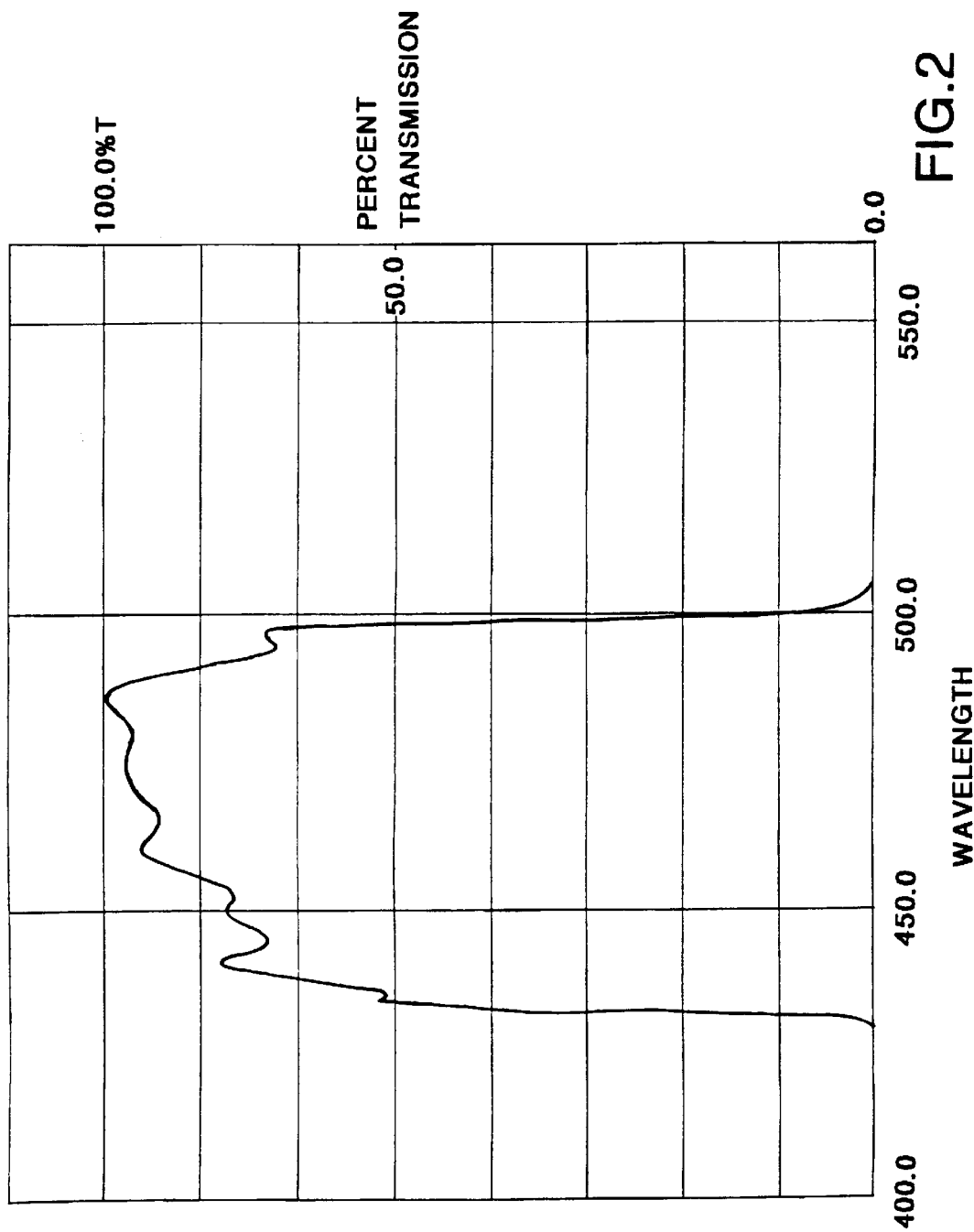
FIG. 2 is an illustration of the relative spectral output intensity of an optical filter used in the present invention.

Filter 127 is used to reject undesirable wavelengths of light and in a preferred embodiment has the characteristics shown in FIG. 2, which illustrates the percent transmission as a function of wavelength. As indicated in this figure, the filter substantially eliminates light with a wavelength below about 430 nanometers and above about 505 nanometers but transmits light between these two wavelengths. Short-arc xenon bulbs produce significant amounts of infrared radiation, which may not be desirable because of the heat generated. An optical filter, such as one with the characteristics shown in FIG. 2, may be placed between the reflector 5 and the light guide to filter out this light. If a reflector without a dichroic coating is used, a separate, dichroic filter may be employed to absorb and dissipate infrared energy. In addition, an index maintaining gel 128 is used to couple light into the light guide. The use of such a gel matches the indexes of refraction at the interface between the filter 127 and light guide to improve the efficiency of the system by maximizing the amount of energy that passes into the light guide 10 and minimizing reflection.

Light guide 10 is made from flexible material, such as a bundle of fiber optic cables housed inside a flexible sheath. In a preferred embodiment, a more flexible, high power, solid state light guide made from a partially polymerized polymer is used, available from Translight of Pomfriet, Conn. Flexibility of the light guide is important to provide the user with sufficient maneuverability of the light guide. Therefore, several feet of light guide are required to provide a sufficient length for normal work conditions.

FIG. 3 shows the relative spectral intensity for a short-arc xenon bulb (model XM1600-27HS manufactured by ORC). As can be seen, this type of arc lamp exhibits a peak in the range of 435–500 nanometers, which comprises both blue and green light.

In a preferred embodiment, the components of the system are mounted in a common housing, appropriately ventilated due to the heat generated by the arc lamp. The light guide is mounted within the housing but protrudes from the housing approximately 6 feet. Within the housing, the lamp, filter, and light guide are sealed to minimize loss of light.

Additional features may also be incorporated into the system of the present invention to improve efficiency. For example, tapered light guides that are larger at the input end may be used to reduce the power density at the interface with the lamp 1. In addition, a wavelength or "lambda" shifter may be used in the light guide to convert ultraviolet light into blue light, thereby increasing the efficiency of the overall system. A lambda shifter may be implemented through the use of a dye inside the light guide. Such dyes may also serve as filters.

As will be apparent to those of ordinary skill in the art, other features may also be incorporated into the system of the present invention in order to provide an easily useable system for the practitioner. For example, for ease of use, a gun-shaped hand piece similar to those used in prior art curing systems (not shown) may be coupled to the end of the light guide through a coaxial bushing to allow for free rotation. In addition, a foot switch (not shown) may be provided to allow hands-free operation of the lamp system. Where a foot switch is used, a holder for the hand piece may be provided with an interlock switch so that the foot switch is enabled only when the hand piece is removed from its holder.

In accordance with the method for curing composite and resin materials of the present invention, the system of the present invention is used in place of prior art curing systems that operate at much lower power levels. The following conversion table shows the energy setting used with a system of the present invention as a function of the composite curing time recommended by the manufacturer of the composite, based on a conventional tungsten halogen curing light with an output power of 500 mW/cm$^2$ and a 0.950 cm$^2$ probe (for a total output power of 475 mW). Also shown in Table 1 are curing times for the system of the present invention, based on a power of 5.0 W at the distal end of the flexible light guide, which is placed proximate the composite to be cured. Power measurements indicate that an output power of 5.0 W or more may be realized at the exit of the light guide if a 1600 W bulb is used. In the system as tested, a short arc xenon bulb was used as described above. The output power at the exit of the light guide will decrease, however, as the system ages and the bulb as well as the light guide degrade.

TABLE 1

Joule Equivalents for Manufacturer Recommended Curing Times

| Recommended Composite Curing Time (for conventional curing light) | Joules for conventional curing light (based on an output power of 475 mW) | Composite Curing Time (for high power arc lamp) | Joule Equivalent (for high power arc lamp) |
| --- | --- | --- | --- |
| 10 seconds | 4.75 | 0.3 seconds | 1.5 Joules |
| 20 seconds | 9.50 | 0.6 seconds | 3.0 Joules |
| 30 seconds | 14.25 | 0.9 seconds | 4.5 Joules |
| 40 seconds | 19.0 | 1.2 seconds | 6.0 Joules |
| 50 seconds | 23.75 | 1.5 seconds | 7.5 Joules |
| 60 seconds | 28.50 | 1.8 seconds | 9.0 Joules |

In order to ensure the proper amounts of energy imparted to the composite, the system of the present invention may be internally calibrated based on energy levels, and a switch provided to select the desired energy output as indicated above. The system will then automatically shut off the lamp after imparting the selected amount of energy. In addition, audible tones may be employed when exposure is initialized and terminated to alert the user.

As is apparent from FIG. 1, the advantages provided by the disclosed system over prior art curing and whitening systems are dramatic. For example, for a composite that requires 40 seconds of cure time using a currently available dental curing light with a tungsten halogen bulb (Demitron Kerr Optilux model 500), it takes only about 1.2 seconds to cure the same composite with the system of the present invention. In addition, as indicated in Table 1, the total energy required is 6.0 J, less than one-third of the 19.0 J required by the prior art curing light. Moreover, composites cured with the system of the present invention provide the same or greater strength values for the composite material. In tests conducted using the present invention, it has been found that the higher power output and resulting shorter curing times are better suited for curing composites, which generally exhibit improved performance the shorter the curing time.

Set forth below are test results comparing the operation of a short arc system of the present invention with a Demitron Optilux 500 Curing Light. Tests were done in accordance with American Dental Association Specification No. 27 (1993 and 1977). In particular, the flexural strength, flexural modulus, and diametral tensile strength of composites cured with both systems were measured. The composite used was L. D. Caulk TPH Universal C2. For the diametral strength tests, 7 samples of composite were tested for each system. Each sample was approximately 0.155 inches in diameter and 0.245 inches in length. The Optilux curing light was used for 30 seconds at 750 mw on each sample, for a total energy of 22.5 J per sample. The short arc xenon system was used for only 0.9 seconds and a total energy of 7.5 J per sample. The table indicates the average load to failure for each of the samples.

The data on flexural strength and flexural modulus constant were compiled from the average of data obtained from five samples each treated with the Demitron curing light and the xenon short arc system. As indicated by the data, the used of the present invention resulted in improved flexural strength (and thus flexural modulus constant N) as well as greater flexibility as evidenced by the lower flexural modulus. The greater flexibility may help lower volumetric reduction stresses within a confined cavity preparation. For these tests, the Demitron curing light was operated with an output power density of 790 mW/cm$^2$ and the short arc xenon system provided a total energy of 4.0 J, both on a sample mold 20×2×2 mm.

|  | Demitron Kerr Optilux 500 | High Power Short Arc Xenon System |
| --- | --- | --- |
| Diametral Tensile Strength | 5486 PSI | 5737 PSI |
| Flexural Strength | 90.38 MPa | 84.33 MPa |
| Flexural Modulus | 4127.7 MPa | 3100.4 MPa |

Tests to determine the safety of the present invention in comparison to the Demitron system indicate that, due to the lower total energy requirements and faster cure times, the use of the present invention results in significantly lower rises in pulpal temperatures. The following table illustrates the pulpal temperature rise for three different samples. For all three samples, the Demitron system was operated for 40 seconds at 600 mW/cm$^2$. For the first sample, the system of the present invention was operated to provide a total of 9.9 J of energy and 5.3 J for the second two samples.

| Sample Parameter | Curing System | Starting Temp F. | Ending Temp F. | Temp Rise F. |
| --- | --- | --- | --- | --- |
| Unaltered Maxillary Canine Tooth | Optilux 40 sec | 67.6 | 76.6 | 9 |
|  | Short Arc 9.9J | 66.7 | 72.3 | 5.6 |
| Buccal Prep 3.1 mm dentin thickness | Optilux 40 sec | 68.7 | 80.4 | 11.7 |
|  | Short Arc 5.3J | 67.9 | 71.5 | 3.3 |
| Buccal Prep 2 mm thick TPH | Optilux 40 sec | 68.3 | 81.2 | 12.9 |
|  | Short Arc 5.3J | 68.8 | 71.4 | 2.8 |

In addition, tests on composite shrinkage stress were also conducted. Theses tests measure the amount of leakage between the tooth structure and the composite. The composite tested was TPH cured with and without a bonding layer. Measurements were made at the incisal and gingivival margins. Results were comparable between the Demitron system and the short arc system of the present invention, but at the gingivival wall, the composite cured by the system of the present invention exhibited less leakage indicating less stress within the composite.

In accordance with the method of whitening teeth of the present invention, the system of the present invention is used in place of existing low power laser and other light sources to accelerate the bleaching of teeth using bleaching compositions. Bleaching compositions using, e.g., hydrogen peroxide, carbamide peroxide, sodium perborate, and other oxygen radical generating agents are well known in the art. Sample compositions are described in commonly assigned, copending patent application Ser. Nos. 08/570,901, filed Dec. 12, 1995, and 08/708,527, filed Sep. 5, 1996, the disclosures of which are incorporated herein by reference. The exposure of these bleaching compositions to light energy, particularly in the blue/green spectrum, accelerates the bleaching effect of these compositions by increasing the amount of free oxygen radicals generated by the dissociation of the composition.

The use of the present invention in place of existing devices for imparting light energy to accelerate the bleaching of teeth provides for a significant reduction in the duration of tooth whitening procedures due to the significantly greater power levels. Each tooth to be treated need be exposed to the light for only a few seconds to impart approximately 24 joules of total energy to the tooth. In addition, the higher rate at which the light energy is provided to the bleaching compositions increases the effectiveness of the composition by converting a greater amount to free oxygen radicals as opposed to molecular oxygen. Furthermore, as for composite and resin curing applications, the pulpal temperature rise will be significantly less as compared with existing, low power systems.

The invention has been described in greatest detail with respect to the particular embodiments and exemplary applications described above. It is understood by those of ordinary skill in the art that changes may be made to the embodiments described herein without departing from the broad inventive concepts thereof. The invention is not limited by this embodiment and examples, but is limited only by the scope of the appended claims.

I claim:

1. A portable, high power arc lamp system comprising:
    a. an arc lamp capable of a power input of at least about 1500 W;
    b. an reflector for reflecting the optical energy generated by said arc lamp;
    c. a flexible light guide for receiving optical energy from said reflector;
    d. a battery for providing electrical power to said lamp;

e. a charging circuit for recharging said battery using 110 V ac power.

2. The system of claim 1 wherein said arc lamp is a short-arc xenon lamp.

3. The system of claim 1 wherein said arc lamp is an argon lamp.

4. The system of claim 1 wherein said reflector is ellipsoidal.

5. The system of claim 1 wherein said light guide is coupled to said arc lamp with an index gel coupling compound.

6. The system of claim 1 wherein said light guide comprises tapered ends.

7. The system of claim 1 further comprising a housing in which said lamp, battery cell, and charging circuit are mounted.

8. The system of claim 1 further comprising an optical filter between said reflector and said light guide.

9. A high power short-arc xenon arc lamp system comprising:
   a. a housing, said housing comprising:
      b. a short-arc xenon lamp capable of a power input of at least 1500 W;
      c. a flexible light guide, the proximal end of said light guide mounted within said housing to receive optical energy from said reflector;
      d. a rechargeable battery for powering said lamp; and
      e. a charging circuit coupled to said battery for recharging said battery.

10. A method of curing a photocurable material comprising:
   a. providing an arc lamp capable of a power input of at least 1500 W;
   b. providing a reflector for reflecting the optical energy generated by said arc lamp;
   c. providing a flexible light guide, the proximal end of said light guide optically coupled to said reflector;
   d. providing a battery for supplying electrical power to said lamp;
   e. providing a charging circuit for recharging said battery cell using 110 V or 220 V ac current;
   f. placing the distal end of said light guide proximate a photocurable material and activating said lamp for a sufficient amount of time to cure said material.

11. The method of claim 10 wherein said arc lamp is a short-arc xenon lamp.

12. The method of claim 10 wherein said arc lamp is an argon lamp.

13. The method of claim 10 wherein said reflector is ellipsoidal.

14. The method of claim 10 wherein said light guide is coupled to said arc lamp with an index gel coupling compound.

15. The method of claim 10 wherein said light guide comprises tapered ends.

16. The method of claim 10 further comprising providing a housing in which said lamp, battery cell, and charging circuit are mounted.

17. The method of claim 10 further comprising an optical filter between said lamp and said light guide.

18. A method of whitening teeth comprising:
   a. providing an arc lamp capable of a power input of at least 1500 W;
   b. providing a reflector for reflecting the optical energy generated by said arc lamp;
   c. providing a flexible light guide, the proximal end of said light guide optically coupled to said reflector;
   d. providing a battery for supplying electrical power to said lamp;
   e. providing a charging circuit for recharging said battery cell using 110 V or 220 V ac current;
   f. placing the distal end of said light guide proximate a tooth for a sufficient amount of time to effect whitening of said tooth.

19. The method of claim 18 wherein said arc lamp is a short-arc xenon lamp.

20. The method of claim 18 wherein said arc lamp is an argon lamp.

21. The method of claim 18 wherein said light guide is coupled to said arc lamp with an index gel coupling compound.

22. The method of claim 18 wherein said light guide comprises tapered ends.

23. The method of claim 18 further comprising providing a housing in which said lamp, battery cell, and charging circuit are mounted.

24. The method of claim 18 further comprising an optical filter between said lamp and said light guide.

25. The method of claim 24 wherein said whitening agent comprises a peroxide compound.

26. The method of claim 18 further comprising applying a whitening agent to said tooth.

27. A method of whitening teeth comprising:
   a. providing an arc lamp for generating optical energy;
   b. providing an ellipsoidal reflector for reflecting the light energy generated by said arc lamp;
   c. filtering the light energy reflected by said reflector with an optical filter to eliminate optical energy with a wavelength below about 430 nanometers and above about 505 nanometers;
   d. providing a flexible light guide, the proximal end of said light guide optically coupled to the output of said filter;
   e. providing a battery for supplying electrical power to said lamp;
   f. providing a charging circuit for recharging said battery cell using 110 V ac current;
   g. placing a bleaching composition on a tooth to be whitened;
   h. placing the distal end of said light guide proximate said bleaching composition and activating said lamp for a sufficient amount of time to whiten said tooth.

28. A method of curing a dental composite comprising:
   a. providing an arc lamp with a power input of at least 1500 W;
   b. providing optical energy generated by said arc lamp to the proximate end of a flexible light guide;
   c. placing the distal end of said light guide proximate a dental curing compound and activating said lamp for a sufficient amount of time to cure said compound.

29. The method of claim 28 further comprising providing a filter to filter out undesired wavelengths of optical energy generated by said arc lamp.

30. The method of claim 28 wherein an ellipsoidal reflector is used to provide optical energy from said lamp to said flexible light guide.

31. A method of whitening teeth comprising:
   a. providing an arc lamp with a power input of at least 1500 W;
   b. providing optical energy generated by said arc lamp to the proximate end of a flexible light guide;
   c. placing a light-activated bleaching compound on a tooth to be whitened;
   d. placing the distal end of said light guide proximate said tooth and activating said lamp for a sufficient amount of time to effect whitening of said tooth.

* * * * *